United States Patent
Klein et al.

(10) Patent No.: US 7,540,847 B2
(45) Date of Patent: Jun. 2, 2009

(54) APPARATUS AND METHOD FOR SELECTIVELY TRANSMITTING VIBRATIONS TO AN INDIVIDUAL SITUATED ON A SUPPORT SURFACE

(76) Inventors: Charles W. Klein, 22 Kolbert Dr., Scarsdale, NY (US) 10583; Peter D. Herger, 620 King St., Port Chester, NY (US) 10573

(*) Notice: Subject to any disclaimer, the term of this patent is extended or adjusted under 35 U.S.C. 154(b) by 747 days.

(21) Appl. No.: 10/759,998

(22) Filed: Jan. 16, 2004

(65) Prior Publication Data

US 2005/0159685 A1 Jul. 21, 2005

(51) Int. Cl.
*A61H 1/00* (2006.01)
(52) U.S. Cl. .................................... 601/46; 601/49
(58) Field of Classification Search .................. 601/46, 601/48–54, 56–62, 65–70, 78, 107, 108, 601/111
See application file for complete search history.

(56) References Cited

U.S. PATENT DOCUMENTS

| | | | |
|---|---|---|---|
| 952,710 A | 3/1910 | Pesce | 340/309.6 |
| 2,460,133 A | 1/1949 | La Pedus | 368/12 |
| 2,580,598 A | 1/1952 | Rody | 368/12 |
| 2,923,122 A | 2/1960 | Inman | 368/12 |
| 2,938,991 A | 5/1960 | Sullivan et al. | 219/528 |
| 3,308,491 A | 3/1967 | Spence | 5/676 |
| 3,417,229 A | 12/1968 | Shomphe et al. | 219/528 |
| 3,585,356 A | 6/1971 | Hall | 5/422 |
| 3,634,655 A | 1/1972 | Jordan | 219/527 |
| 3,786,628 A | 1/1974 | Fossard et al. | 368/12 |
| 3,968,530 A | 7/1976 | Dyson | 5/676 |
| 4,162,393 A | 7/1979 | Balboni | 219/217 |
| 4,423,308 A | 12/1983 | Callaway et al. | 219/217 |
| 4,659,905 A | 4/1987 | Gabrosek et al. | 219/212 |
| 4,690,960 A | 9/1987 | Yamauchi | 523/442 |
| 4,707,872 A | 11/1987 | Hessel | 5/676 |
| 4,783,866 A | 11/1988 | Simmons et al. | 5/639 |
| 4,788,730 A | 12/1988 | Bexton | 5/676 |
| 4,798,936 A | 1/1989 | Johnson | 219/217 |
| 4,958,627 A | 9/1990 | Park | 601/49 |
| 5,054,145 A | 10/1991 | Tsuchiya et al. | 5/655.5 |
| 5,076,260 A * | 12/1991 | Komatsu | 601/59 |
| 5,144,600 A | 9/1992 | Cheng | 368/12 |
| 5,437,608 A * | 8/1995 | Cutler | 601/49 |
| 5,590,430 A | 1/1997 | Sereboff | 5/655.5 |
| 5,636,395 A | 6/1997 | Serda | 5/691 |
| 5,686,882 A | 11/1997 | Giani | 340/407 |
| 5,737,692 A | 4/1998 | Lang | 455/66.1 |
| 5,764,594 A | 6/1998 | Berman et al. | 368/12 |
| 5,836,900 A * | 11/1998 | Leventhal | 601/57 |
| 5,894,455 A | 4/1999 | Sikes | 368/12 |
| 6,037,403 A | 3/2000 | Katase et al. | 524/579 |

(Continued)

*Primary Examiner*—Michael A. Brown
(74) *Attorney, Agent, or Firm*—Lerner, David, Littenberg, Krumholz & Mentlik, LLP

(57) ABSTRACT

An apparatus and method of using directed and isolated vibrations for awakening, alerting, or massaging a designated person situated on a support medium without disturbing another person in the vicinity. The vibrations from the vibrating mechanism are dampened by suitable material located between the vibration mechanism and the support medium. The vibrating device of the invention can be activated by various predetermined conditions such as time, safety or burglar alarms and the like. It may also be used as a selective massaging device which can deliver a massage to the user without disturbing another person situated on the same support medium.

39 Claims, 3 Drawing Sheets

U.S. PATENT DOCUMENTS

| | | | |
|---|---|---|---|
| 6,077,238 A | 6/2000 | Chung | 601/57 |
| 6,087,942 A * | 7/2000 | Sleichter et al. | 340/576 |
| 6,151,278 A | 11/2000 | Najarian | 368/12 |
| 6,210,351 B1 | 4/2001 | Korenaga | 601/148 |
| 6,252,336 B1 | 6/2001 | Hall | 310/339 |
| 6,448,677 B1 | 9/2002 | Won | 310/81 |
| 6,502,264 B1 | 1/2003 | Clothier et al. | 5/915 |
| 6,522,037 B2 | 2/2003 | Lee et al. | 310/68 R |
| 6,560,802 B2 | 5/2003 | Fujii | 5/639 |
| 2002/0078503 A1 | 6/2002 | Godette | 5/600 |
| 2002/0091340 A1 | 7/2002 | Robbins | 601/46 |
| 2002/0111572 A1 | 8/2002 | Waters | 601/57 |
| 2003/0121104 A1 | 7/2003 | Bretschger et al. | 5/694 |
| 2003/0135930 A1 | 7/2003 | Varese et al. | 5/727 |
| 2005/0148807 A1* | 7/2005 | Salkinder et al. | 600/9 |

\* cited by examiner

APPARATUS AND METHOD FOR SELECTIVELY TRANSMITTING VIBRATIONS TO AN INDIVIDUAL SITUATED ON A SUPPORT SURFACE

BACKGROUND OF THE INVENTION

1. Field of the Invention

The present invention relates to a device and method for directing and isolating vibrations to a designated person situated: on a support surface without disturbing any other person in the vicinity, including another person situated on the same support surface, said vibrations for awakening, alerting, or warning a designated person when a predetermined condition has been detected or for massaging the designated person.

2. Discussion of the Prior Art

It is most common to use an audible alarm to awaken or alert an individual of the occurrence of an event or a predetermined condition. However, where two or more persons are sleeping or resting in close vicinity, and only one of the persons desires to be awakened at a predetermined time or by other circumstances, a quiet alarm is needed. It has been suggested to utilize vibrations rather than audible sounds. For example, U.S. Pat. No. 2,460,133 describes the use of vibrations to awaken an individual without disturbing others in dormitories and in sleeping quarters for military and naval forces. According to that patent, a vibrator is placed under cushions or under a mattress to awaken the one person sleeping on the mattress. Other suggestions of a vibration mechanism for a bed are described in U.S. Pat. No. 6,210,351 (water bed), U.S. Pat. Nos. 6,502,264 and 5,076,260. However, when it is desired to awaken or alert only one of two people sleeping on a bed, vibrating the bed as described in these patents would not achieve the objective, since both persons in the bed would be aroused by the vibration.

Another approach that has been suggested is to associate or attach the source of vibration to the person designed to be awakened. This could have the effect of reducing the vibrations from affecting another person on the same support medium. For example, U.S. Pat. No. 5,144,600 describes a vibrating device incorporated in or under a pillow. Such a device can be uncomfortable during sleep and may be hazardous, particularly if it has a hard-wire connection. Another disadvantage of such a device is that as a result of a person's normal movements during sleep, the pillow can be dissociated from the person or disconnected. Another example of a device attached to the person is a vibrating earpiece, such as that described in U.S. Pat. No. 5,737,692. Again, this type of vibrating device is uncomfortable, can be dislodged during sleep and depends on the user remembering to install the ear piece for each use. Furthermore, due to its size, it can be easily misplaced. U.S. Pat. No. 5,686,882 describes a vibrating device worn on a person's wrist. The disadvantages of this device are similar to those of the earpiece device, in that individuals may find such devices uncomfortable to wear, susceptible to dislodgment while sleeping and may be forgotten when going to sleep.

Therefore, there is a need for an alarm or alerting device that is capable of directing vibrations to the targeted individual on a support medium without disturbing another in the vicinity or on the same support medium, where such device is convenient, cost-effective, comfortable and reliably utilized.

SUMMARY OF THE INVENTION

The present invention seeks to provide a reliable and convenient device and method for selectively transmitting vibrations to a designated person on a support medium without disturbing any other person in the vicinity, including a person on the same support medium as the designated person.

The present invention further provides a silent alarming device for awakening or alerting a designated individual on a bed or other support medium by selectively transmitting vibrations to that individual without disturbing any other person in the vicinity, including a person on the same support medium.

The present invention also provides a device for selectively transmitting a vibrating massage to a designated individual on a support medium, without disturbing any other person in the vicinity, including a person on the same support medium, whereby the device is optionally capable of automatically turning off at a preselected time.

An object of the invention is to provide a device that can be associated or attached to a bed or other medium supporting an individual, rather than a device that must be worn by the individual or installed by the individual at each use. While associated with the support medium, it is desired that the device not be a permanent attachment to the bed or other support medium and can be separately acquired and installed. In a further embodiment the device is portable and removable so that it can be used with portable support media, such as cot beds, inflatable mattresses, futon sleeping furniture, chairs, sleeping bags and the like. The removable aspect of this embodiment enables the device as well as the support medium to be easily cleaned. Additionally, the device of the invention can be covered with a vinyl, rubber or other water-resistant or water-proof material to further aid in cleaning.

A further objective is to provide a device that is capable of transmitting vibrations to awaken or alert a designated individual on a support medium yet have the vibrations substantially insulated or dampened to minimize transmission of the vibrations to another person in the vicinity of or on the same support medium as the designated individual.

Another objective is to use the device of this invention in various methods for alerting or awakening a designated person who is sleeping or resting on a support medium, without disturbing any other person in the vicinity, including a person on the same support medium, of the existence of one or more predetermined conditions, such as: a sound from a remote location, e.g. a crying infant; bed-wetting by the designated or another person; activation of a security, fire or smoke alarm; a doorbell; a telephone call; and activation of a motion sensor.

DETAILED DESCRIPTION OF THE INVENTION

Figure 1:
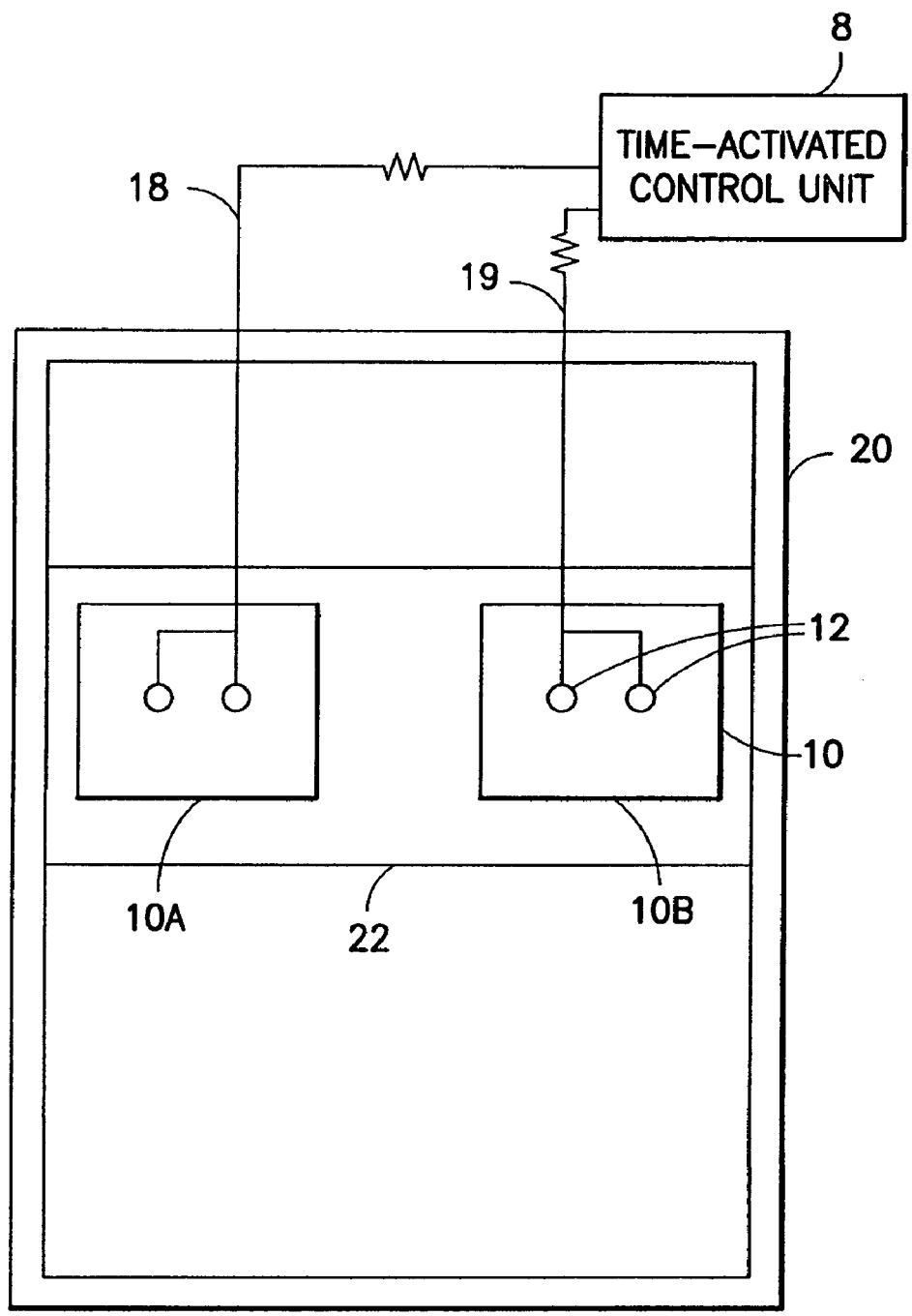
FIG. 1 illustrates an overhead view of an alarm device of the present invention comprising two vibrating members for separate operation by two users sharing a queen-sized bed.

One embodiment of the present invention is a selective alarm device for awakening or alerting a designated person or user situated on a support medium, of the existence of a predetermined condition without disturbing any other person in the vicinity of the user, said device comprising: (i) a vibrating member comprising a vibration mechanism and at least two regions, a vibration transmission region and a vibration dampening region, said vibration transmission region substantially located between the vibration mechanism and the surface of the vibrating member nearest the user's body and said vibration dampening region substantially located between the vibration mechanism and the surface of the vibrating member nearest the support medium; (ii) a sensor/controller comprising one or more elements which function as a sensor and controller, being capable of detecting the presence of a predetermined condition, and upon detection of the condition causing the activation of the vibration mechanism incorporated within the vibrating member; and (iii) one or more power sources for operating the constituents of the device including the sensor, the controller and the vibration mechanism; said vibration mechanism when activated being capable of creating vibrations sufficient to alert or awaken the user; said vibration transmission region having a density greater than that of the vibration dampening region; said vibrating member being sufficiently flexible so as not to be uncomfortable to the user when situated between the user and the support medium and being of a sufficient size and dimension to enable the vibration mechanism therein to transmit vibration in sufficient intensity to awaken or alert the user while dampening transmission of vibration to the support medium to prevent the disturbance of another person on the support medium.

Another embodiment of the present invention is a selective vibrating device for use on a bed or chair or other furniture which supports a user's body, said selective vibrating device comprising a vibrating member and a power source, said vibrating member comprising a vibration mechanism and at least two regions, a vibration transmission region and a vibration dampening region, said vibration transmission region substantially located between the vibration mechanism and the surface of the vibrating member nearest the user's body and said vibration dampening region substantially located between the vibration mechanism and the surface of the vibrating member nearest the support medium; said vibration mechanism when activated -and powered by said power source being capable of creating vibrations sufficient to alert or awaken the user; said vibration transmission region having a density greater than that of the vibration dampening region; said vibrating member being sufficiently flexible so as not to be uncomfortable to the user when situated between the user and the support medium and being of a sufficient size and dimension to enable the vibration mechanism therein to transmit vibration in sufficient intensity to awaken or alert the user while dampening transmission of vibration to the support medium to prevent the disturbance of another person in the vicinity or on the same support medium.

The present invention additionally embraces an apparatus for the targeted communication of a vibration alert to a user, comprising a vibrating unit, a high transmission material substantially encasing the vibrating unit and a low transmission material in contact with a portion of the high transmission material's surface, such that the low transmission material provides a dampened signal path and wherein vibration of the vibrating unit transmits the alert to the user through exposed surface of the high transmission material.

The present invention also includes a method for awakening or alerting a user situated on a support medium without disturbing anyone else in the vicinity, including another person on the same support medium as the user, said method comprising using the selective alarm device or selective vibrating member as described immediately above.

In accordance with the invention, the selective vibrating member can also be adapted to be utilized as a selective massaging device for providing a massage to a user situated on a support medium, without disturbing another individual in the vicinity of the user. When used as a selective massaging device, the vibrating member should be capable of providing a range of vibration configurations, differing in amplitude and frequency, with a control to enable the user to modify the intensity and nature of the massage. The selective vibrating member, when used to provide a massage, can also be controlled with a timer to automatically turn it off after a preselected time.

The alarm or alerting device of the present invention is capable of being activated by a variety of different predetermined conditions. Most preferable is a time-activated alarm, whereby the activating condition is a preselected time. The sensor for detecting such a condition includes a time-keeping device, which can be programmed for the preselected alarm time. Also contemplated is a microprocessor/microcontroller which can be programmed with one or more desired wake-up or alarm times. When a match occurs between the preprogrammed alarm time and the time of day, the microprocessor/microcontroller activates the vibration mechanism via a hard wire or through a wireless transmitter to a receiver associated with the vibration mechanism. In another embodiment, the controller or microprocessor can initiate the operation of the vibration mechanism by directing power to the vibration mechanism.

The time-activated alarm has several applications in addition to a morning wake-up alarm. The device can be preprogrammed for a time to awaken a user for taking medication or monitoring one's condition, e.g. blood sugar, without disturbing another person sleeping on the same bed. The time-activated alarm of the present invention can also be programmed to awaken a user at a predetermined time, such as a child being toilet trained or an adult suffering from bed soiling or enuresis, without disturbing another person in the vicinity of the user. Use of the alarm device in this manner can enable such persons to use the bathroom prior to a bedwetting incident without disturbing others in the vicinity.

Another predetermined condition for activating the alarm or alerting device of the present invention is an audible sound originating from a remote location such as a doorbell, a ringing telephone or a crying infant. A decibel or other noise monitor located in the vicinity of the source of the sound can be adapted to detect the sound and upon such detection, transmit a signal or sound to the sensor/controller, resulting in the activation of the vibration mechanism. In this embodiment the device detecting the sound can be directly connected to the sensor/controller of the device of the invention, or transmit a signal or transmit a private sound (not audible to the user) to the sensor/controller. Also contemplated is the direct connection of the sensor/controller of the device to the source of the activating condition, such as a telephone or doorbell. Therefore, the audible sounds of the ringing phone or doorbell can be turned off, and the controller can be activated by its direct connection to the doorbell or phone. In this embodiment of the method and device of the invention, only the user of the device would be alerted or awakened by a telephone call, a crying infant or a doorbell, and other persons in the vicinity would not be disturbed.

The controller can also be activated by various security and safety devices such as smoke alarms, carbon monoxide monitors, flood/water detection devices, motion detectors, and burglar alarms. This is particularly useful if the user of the device of the invention has a hearing handicap but is able to be alerted by vibration.

The device of the invention can also be adapted to aid an individual suffering from bed-soiling during sleep. The device of the present invention can be adapted with a sensor to detect humidity or water occurring from a bed-wetting incident. Upon detecting this determined condition, the vibration mechanism would be activated and the user, who can be the individual suffering from the bed-soiling and/or another, e.g. a care taker, would be awakened without disturbing others in the vicinity. The user of such a device can be a young child being toilet trained or an adult suffering from enuresis or a side-effect of medication or other illness and/or a person caring for such individual. Therefore, the present invention provides a method for alerting an individual of a bedwetting incident without disturbing another person in the vicinity, said method comprising use of the alerting device of the present invention wherein it is adapted to activate the vibrating mechanism when moisture or water is detected.

The alarm device of the present invention can also be used in a method to alert or awaken persons with a hearing handicap, not only by a predetermined time, but also by other conditions such as a telephone call, activation of a fire alarm, burglar alarm, baby monitor or other safety and protection devices. The device can be connected to or incorporated into an existing alarm system in a building. Upon the sensing of an emergency or safety condition, the device can vibrate at great intensity to forcibly shake a user to alert him or her to the presence of such condition.

It is not required that the device of the present invention include a sensor element, separate from the controller. As discussed above, some activating conditions can be transmitted to, and detected directly by, a controller device.

The controller can be capable of not only receiving signals from various separate sensor devices but also should be capable of being directly activated by other devices, such as by the low voltage output of a doorbell or telephone line or by a signal generated by a safety or protection device. The controller can be activated in a manner similar to a telephone answering machine or facsimile machine whereby activation occurs by an incoming phone call and not by the audible sounding of a phone.

In a particularly advantageous embodiment, X10 is used to actualize the smoke alarms, fire alarms, remote temperature sensor systems in current home automation technology. X10 is a communications "language" that allows compatible products to talk with each other using existing electrical wiring in the home. X10 technology is described in the following United States Patents, each of which is incorporated herein by reference: U.S. Pat. Nos. 4,189,713, 4,200,862, 4,628,440, 4,638,299 and 5,005,187.

The X10 signal is superimposed over household current. The signal is sent at the moments in the alternating current cycle when voltage is 0. This is because standard AC operates at 60 hz, so there are standard inverval pauses in the current delivery cycle. The X10 sends a unique signal to each device on which there is a controller and receiver unit configured to receive it. Each device has a unique signal or address that only it can identify (similar to a computer's distinct IP address in a network). The controlling and receiving units are myriad, but the important point is that they can use X10 protocol to communicate remotely with one another.

Another communications standard for home automation is CEBus, or Consumer Electronic Bus, which was developed for consumer electronics in the home. It operates over the 110V AC powerline (PLC), twisted pair (TP) cable, coax cable, RF -and Infrared. It is presently more expensive than X10, however, it is a faster, more efficient communication protocol.

It is preferable that the controller be programmable by the user to customize various preselected options for the operation of the vibration mechanism. For example, the controller can have the capability of controlling the electrical output to the vibration mechanism or otherwise control the operation of the vibration mechanism to enable the user to preselect the amplitude and/or frequency of the vibrations generated during the alarming cycle. The controller also can have the capability of causing the vibration mechanism to change the amplitude and/or frequency of the vibrations during the alerting or massaging cycle. Different vibration patterns can be programmed to correspond to specific preconditions, e.g., one vibration pattern for security breach and a different vibration pattern for time-awakening. A gradual increase in the intensity of the vibration transmitted to the user over an alarming cycle allows for a minimum intensity vibration to arouse the light sleeper, and more intense vibration if the initial vibration is not sufficient to arouse the user. When used as a selective massage device, it is desirable to be able to vary the amplitude and/or frequency of the vibration to provide a variety of massage techniques and sensations.

The controller also can be adapted to provide a backup audible alarm if the user fails to intervene to switch the alarm off after a preset time period of an alarm cycle. Other techniques for awakening an individual can be incorporated in the device to assure the user is awakened. For example, the device can be adapted with a source of light or a source of smell to function simultaneously with the vibration or as a backup for the vibration alarm. Also, the controller can be programmed to have a snooze feature, enabling the user to intervene and terminate vibration for a preset "snooze" period of time, with the vibration resuming after the preset snooze period. The controller can additionally be programmed to have a "light snooze" feature, enabling the user to lower the intensity of the vibrations for a short period before resuming alerting vibrations.

Throughout the description of the present invention it should be understood that the various elements can be interconnected by hard wire or by wireless transmissions via radio waves, infrared and the like.

The device further can incorporate a self-abatement feature, whereby the alarming or alerting mechanism will shut itself off after the elapse of a predetermined amount of time, if the user does not manually turn it off. Such a feature is useful if the user forgets to turn off the mechanism. By this feature, any backup alerting mechanism such as an audible alarm will similarly be turned off.

The device of the present invention can be powered by several alternative sources. There can be a single electrical connection to the controller, which, by one or more hardwire electrical connections, provides power to operate any sensor and the vibration mechanism. Alternatively, the device can be powered by several independent connections to one or more power sources, including a combination of battery power and electrical outlet power. For example, the sensor can be powered by battery and the vibrating motor or mechanism powered by house current. In yet another embodiment, the vibration mechanism can incorporate a weight detector, wherein the mechanism will not operate unless the user's body is detected as pressed upon the vibrating member.

In a preferred embodiment, the vibrating member is a separate accessory, which can be added to a bed or other support medium, on the surface or under throws or slipcovers of a chair or sofa or under sheets and pads of a bed. In another embodiment of the invention, a vibrating member is contained within or made part of the essentially fixed portion of the bed or other support medium, such as within the mattress of a bed or the seat or back of a sofa or chair. In a further embodiment the vibrating member can be part of a mattress pad, sofa liner or bed sheet or pad. In each of these embodiments, the vibrating transmission surface should be situated near or on the surface of the bed or other support medium to enable proper transmission of the vibration to the user.

In accordance with the invention, when the vibrating member is used in an alerting or alarming device it should be situated to enable transmission of the vibration to an area of the user's body that is sensitive to vibration and an area of the body that consistently remains located near the vibrating member during the user's sleeping period. The user can vary the location of the body to target the vibrations. In accordance with the invention, it is preferred to locate the vibrating member so as to target transmission of vibrations to the torso or midsection of the user, which is one of the least mobile areas of the body when sleeping. Preferably it is desired to target the lower torso which is meant the lower midsection of the body, including the abdomen, sides and lower back.

Targeting the torso takes advantage of scientific and ergonomic factors. According to Dr. Samuel Dunkell in his book *Sleep Positions: The Night Language of the Body,* most individuals tend to sleep in one or more of four sleep positions, which are the full fetal, the semi-fetal, the royal, and the prone positions. In each of these positions, and their various subtypes, a portion of the torso region, especially the lower torso region, is in some contact with the sleeping surface. Moreover, as a sleeper's body moves through these various sleeping positions in the course of a night's sleep, the torso tends to dominate substantially the same area of the sleeping-surface, e.g. the torso moves relatively little from the starting contact area of the sleeping surface. This makes the torso region an ideal target where the vibrating member is associated with the sleeping medium.

Another ergonomic advantage of targeting the torso is that if an individual sleeps in a position with the head elevated, with greater pillow support, either by preference or because of medical conditions such as sleep apnea or cardiac issues, the torso will still be in contact with the sleeping surface. As such, it is appropriate to target the torso region with vibrations to most consistently and effectively awaken individuals when sleeping.

There is a significant economic benefit in targeting only one area of the body. This minimizes the size required for the vibrating member, the number of vibrating mechanisms and avoids the use and expense of large and cumbersome devices that target multiple body parts or the entire body in order to alert or awaken the user. By minimizing the amount of vibration generated, it reduces the vibration that must be dampened to avoid disturbing another in the vicinity. A person can be effectively alerted or awakened by vibratory pulses on only one part of the body. As such, there is no significant benefit to targeting multiple areas. The device of the present invention, which can awaken a sleeping person when transmitting vibrations to a limited portion of the body, is a more cost-effective and a more efficient device.

Conventional methods can be employed to maintain the vibrating member at the proper location on the support medium to transmit vibration to the desired portion of the user's body. For example, the vibrating member can be adapted to have conventional accessories to limit the movement of the vibrating member, such as hook and loop fasteners, glue, straps, sewing, or staples. In another embodiment of the invention the vibrating member can be secured to a damping material in the shape of a strip of material, which can be removably attached to the bed or other support medium or accessory to maintain the position of the vibrating member.

In a further embodiment of the invention, the device can comprise two or more vibrating members, each positioned to transmit vibration to different parts of a user's body or to separate users on the same support medium or on support media in close vicinity. When multiple vibrating members are used, they can be separately controlled for operation. When separate vibrating members are employed for multiple users on a support medium or on support media in close vicinity, each individual in the support medium can separately program the circumstances and conditions for being awakened or alerted. This embodiment can use one controller for a plurality of vibrating members, or there can be a controller and one or more separate auxiliary controllers. It is preferred to locate an auxiliary controller to be conveniently accessible to the second user for control of the second vibrating member. When multiple vibrating members are used as selective massage devices, the independent controller allows each user separately to control or modify intensity and other operations of the vibrating mechanism.

The vibrating member contains a vibration mechanism and is composed of or associated with materials of varying degrees of density. As described above, the vibration transmission region has the highest density of materials that compose the vibrating member and is substantially located between the vibration mechanism and the surface of the vibrating member that is nearest the user's body. Lower density material is utilized in other regions of the vibrating member to dampen and absorb vibration, to minimize the vibration that is transmitted to the support surface, which can lead to disturbing another person on the same support medium.

In one embodiment, the vibration mechanism and other component parts can be added or removed from the vibrating member. This allows for easy replacement of batteries or replacement of the mechanism itself should it fail to work or break. This embodiment additionally enables easy cleaning of the vibrating member, since the electrical components of it may be removed.

There are several factors that must be considered in determining the overall thickness of the vibrating member. First, the vibration dampening region must possess sufficient dimension between the vibration mechanism and support medium to adequately dampen vibrations to prevent disturbance of another person on the same support medium. A second important factor is comfort for the user which requires a sufficient thickness to encompass the depth dimension of the vibration mechanism when the user is actually above the vibrating member. The vibrating member should be thick enough to be comfortable to the user but not too thick to prevent adequate transmission of vibrations to the user. A further benefit of the vibration damping region is that it will attenuate any noise associated with the operation of the vibration mechanism.

In one embodiment, a vibrating member, without the user situated thereon, can have a thickness of less than about one inch, but the vibrating member will have a reduced thickness when it is compressed from the weight of the user. For construction purposes, the vibration mechanism can be located at a uniform distance between the transmission and support surfaces, but it is preferable to place the vibration mechanism as close as practical to the surface of the vibrating member that is nearest to the user. The vibrating member can include any number of vibration mechanisms and the vibrating member can be adapted to separately operate any one or more of the vibration mechanisms.

A preferred material for the vibration transmission region of the vibrating member is a dense, viscous solid polymeric material such as a soft, flexible synthetic rubber, a viscoelastic polymer, a cross linked polyurethane gel and a glycerin gel. Examples of such materials include the product known as Akton® visco-elastic polymer, manufactured by Action Products and Xcelgel™ cross-linked pliable polymer, manufactured by Polymer Concepts, Inc. Such materials not only can provide efficient transmission of vibration to the user but can more broadly distribute and transmit the vibration to a wider cross-sectional area of the user's body, than that of the vibrating mechanism itself.

The vibrating member includes a region of material less dense than the vibration-transmission region for dampening or absorbing vibration, functioning to isolate the vibrations in the denser material region of the vibrating member. A further advantage of the vibration damping region is that it attenuates any noise resulting from the vibration mechanism. The damping region containing less dense material can be located along substantially the entire lower support surface of the vibrating member or only along a portion of the support surface. Alternately, the damping region can also be located as multiple regions in the vibrating member, each region associated with each vibrating mechanism.

The less dense region can be directly included within the vibrating member or can be associated with the vibrating member as a separate element. For example, the most dense vibration transmission region can be bonded to a less dense material, which functions to dampen the vibration. Alternatively, the vibrating member may comprise two discreet, unattached portions, the denser, vibration transmission region would incorporate the vibration mechanism and it would be placed above the separate damping material, whereby the damping material would be between the vibration transmission region and the surface of the support medium.

According to the present invention, the damping of vibrations is achieved by damping the vibrations generated by the vibration mechanism with a relatively low density material located in at least part of the region between the vibration mechanism and the surface of the support medium. Damping has been described as a physical property relating to an oscillating system returning to its equilibrium state as quickly as possible. It is important to choose a material for the damping region that achieves sufficient damping in the volume of material present in the vibrating member to minimize the vibration transmitted to the bed or other support surface which can reach another person and disturb that other person. The material must not only have this important damping property but also possess reasonable levels of durability and comfort needed for a support medium. The material should also be effective at absorbing the vibration energy, such as by resistance to fluid movement.

A suitable damping material is open-celled, flexible polyurethane foam (FPF). A particular density-of the damping material is not critical, except that it must be less dense than the material in the vibration transmission region and there must be a sufficient volume of the damping material to provide the desired damping effect. While not critical, a preferred material has a density in the range of about 1.3 to 1.8 pounds per cubic foot. Other suitable damping materials include short staple polyester fiber, cotton and down. Desirable damping can be achieved, for example, where the difference in density between the highly dense material and damping regions is about 60.00 pounds per cubic foot. Such a material can be bonded or glued or adhered to the more dense material of the vibrating member or can be a removable support, lying between the vibrating mechanism and the surface of the bed or other support medium, and optionally extending in directions beyond the surface of the vibrating member.

The source of vibration in the vibrating member is any conventional motor or other mechanism which has a suitable shape for being included in the vibration member and has a sufficient output of vibration, in terms of amplitude and frequency to alert or awaken or massage a person. One or more vibration mechanisms can be included in the vibrating member. The preferred embodiment uses vibration motors of a shape such as a pancake or cylindrical shape to ensure comfort. Illustrative vibration motors are those included in cell phones and various massaging devices. Such motors can be adapted to be used in the vibrating members of the present invention. Most common of these vibrating motors are those that rotate an eccentric weight in an electromagnetic field. Another class of vibrating mechanisms useful in the present invention are those made of piezoceramics, wherein a piezoelectric crystal vibrates when an alternating voltage is applied to it. Examples of suitable vibration mechanisms include, but are not limited to, those described in U.S. Pat. Nos. 6,448,677, 6,522,037 and 6,252,336, each of which is incorporated herein, by reference.

DETAILED DESCRIPTION OF THE DRAWINGS

The apparatus and method according to the present invention enables a host to be alerted, awakened, or massaged by the use of vibrations, while those vibrations are sufficiently dampened and insulated to minimize disturbance of another person in the immediate vicinity.

FIG. 1 illustrates an overhead view of an alerting system embodiment of the invention. FIG. 1 comprises two vibrating members 10A and 10B for each of two persons lying on a queen-sized bed 20, which is 60 inches wide. The vibrating members 10A and 10B are powered by and connected to controller 8 by hard-wire connectors 18 and 19, respectively. Vibrating members 10A and 10B are placed at least about 18 inches apart. The vibrating members lay over a damping material comprising an open-celled polyurethane material in the shape of a strip 22. The damping section located below each vibrating member and in the at least 18-inch separation area between the vibrating members provides a damping section which tends to absorb and isolate vibrations in order to reduce the intensity of vibrations transmitted from each vibrating member to the other person on the bed. Vibrating members 10A and 10B each contain a vibration mechanism, which comprise two pancake-shaped conventional vibrating motors 12. Vibrating members 10A and 10B are secured to the damping polyurethane strip by hook and loop fasteners or other securing means to ensure that the vibrating members remain in place in the area of the torso region of the respective user.

Controller 8 is a standard electrical unit, which is programmed either by the manufacturer or the sleeper to separately control the two vibration members. A sensor-activated system is incorporated in the controller 8. The controller 8 depicts a time-activated sensor, which is programmed to detect a predetermined time.

Figure 2A:
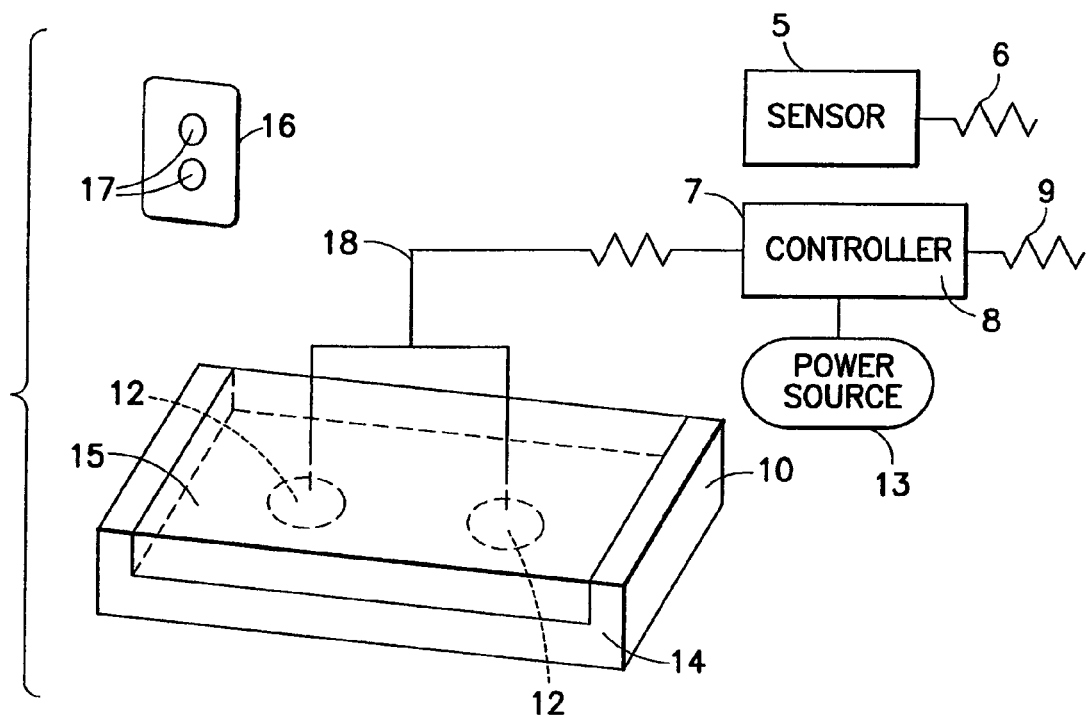
FIG. 2 is a top-view (A) and side-view (B) of a vibrating member 10 of an alarm device of the present invention.
Figure 2B:
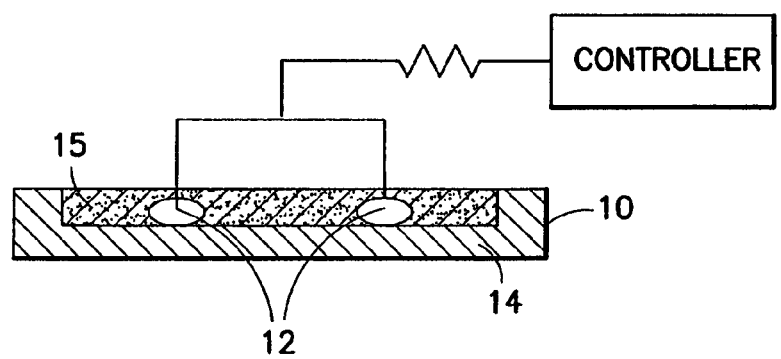

FIGS. 2A and 2B illustrate an overhead view and side view, respectively, of vibrating member 10 in accordance with the present invention. Vibrating member 10 contains a vibration mechanism 12, which comprises a plurality of pancake shaped vibration motors 12 embedded in a highly dense substance 15. Vibrating member 10 has a uniform thickness. The composition of the dense material 15 adjacent the motor is a soft, flexible synthetic rubber 15. A second region in the vibrating member 10 comprises a less dense material 14 damping the vibration from the motors to reduce the transmission of the vibration to the underlying bed or furniture surface. The less dense damping region 14 is composed of a flexible polyurethane material.

Each vibration mechanism 12 is located closer to the transmission, upper surface of vibrating member 10. Also, to ensure maximum vibration transmission to the user, while retaining comfort, each vibration mechanism 12 is located at a uniform distance from the upper surface of vibrating member 10 and symmetrically centered, as shown. Vibration mechanism 12 is a conventional vibrating motor such as found in cell phones or massagers. Preferably vibration mechanism 12 is a pancake shape in order to fit within the vibrating member and ensure maximum comfort.

Vibration mechanism 12 is connected to the controller 8 via conventional hard wires 18. The vibration mechanism 12 receives its power from the hardwire connection to the controller 8. The controller 8 is connected by another hard wire to a power source 13. The controller 8 communicates by a wireless receiver 9 with the sensor 5 and its transmitter 6. The controller 8 also communicates by wireless transmission with a remote user switch 16. The remote user switch 16 has buttons 17, which can turn off an activated alarm and can activate a snooze cycle by transmitting a signal to the controller 8. The controller 8 has a control panel 7 which enables a user to program the time, set one or more times for activation of the alarm and to enable one or more sensor connections.

Figure 3:
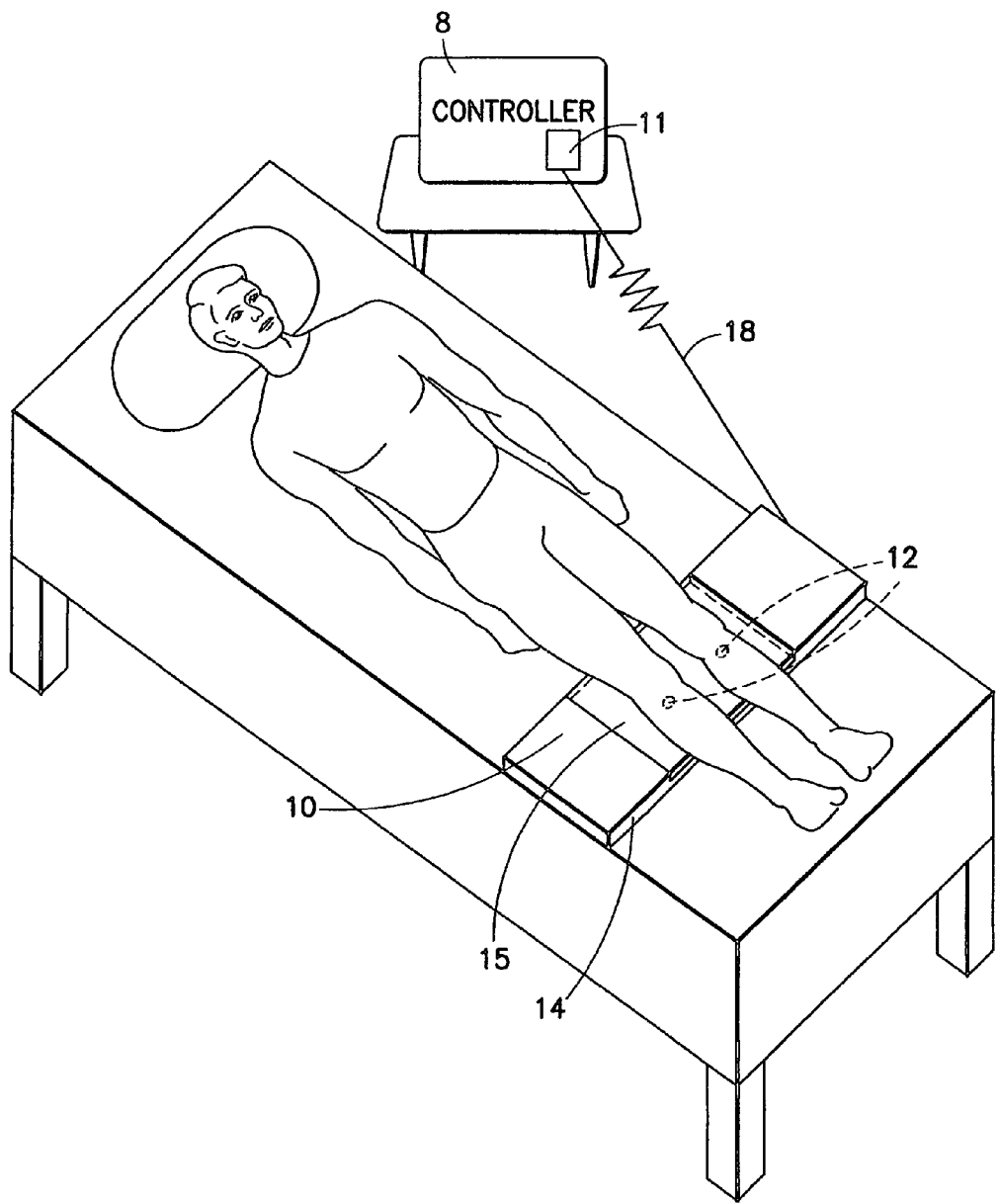
FIG. 3 illustrates an alternate embodiment of the device of the present invention for use as a selective massaging device.

FIG. 3 illustrates an alternative embodiment of the invention wherein the vibrating device is used as a selective massaging device. Vibrating member 10 contains a vibration mechanism, which comprises vibration motors 12. Immediately surrounding the vibration mechanism is a higher dense material 15, which is itself surrounded on three sides by a lesser dense substance 14. The vibrating device is connected to the controller 8 via hard wire connector 18. Controller 8 comprises an activation switch 11, which can be set to activate the vibrating device to produce vibrations at various levels of intensity and/or with different patterns of vibration. The vibrating member 10 is not fastened to the resting surface, and can thus be placed in any location desired by the user, giving a relaxing massage directed at any specific part of the body desired. In this Figure the massage is directed at the lower leg area of the user.

The many features and advantages of the present invention are apparent from the detailed specification, and thus, it is intended by the appended claims to cover all such features and advantages of the invention which fall within the true spirit and scope of the invention.

Furthermore, since numerous modifications and variations will readily occur to those skilled in the art, it is not desired that the present invention be limited to the exact instruction and operation illustrated and described herein. Accordingly, all suitable modifications and equivalents that may be resorted to are intended to fall within the scope of the claims.

We claim:

1. A selective alarm device for use on a support medium for awakening or alerting a user situated on a support medium of the existence of a predetermined condition without disturbing any other person in the vicinity of the user, including another person situated on the support medium, said device comprising:

(i) a vibrating member for use in a location between a support medium and a user situated on the support medium, comprising a vibration mechanism, a vibration transmission region and a vibration dampening region, said vibrating member comprising two primary surfaces, a surface designated for facing the upper portion of the support medium and a surface designated for location nearest the user situated on the support medium, said vibration mechanism when activated being capable of creating vibrations sufficient to alert or awaken the user;
   said vibration transmission region being composed of a material that provides efficient transmission of vibration through the material and being substantially located between the vibration mechanism and the surface of the vibrating member designated for location nearest the user's body; and
   said vibration dampening region being composed of material that tends to reduce or dampen the transmission of vibration through the material compared to the transmission region and being located between the vibration mechanism and the surface of the vibrating member designated for facing the upper portion of the support medium;

(ii) a sensor/controller comprising one or more elements which function as a sensor and controller, being capable of detecting the presence of a predetermined condition, and upon detection of the condition causing the activation of the vibration mechanism incorporated within the vibrating member; and (iii) one or more power sources for operating the constituents of the device including the sensor/controller and the vibration mechanism;

said vibration mechanism when activated being capable of creating vibrations sufficient to alert or awaken the user; said vibration transmission region having a density greater than that of the vibration dampening region; said vibrating member being sufficiently flexible so as not to be uncomfortable to the user when situated between the user and the support medium and being of a sufficient size and dimension to enable the vibration mechanism therein to transmit vibration in sufficient intensity to awaken or alert the user while said vibration dampening region dampens transmission of vibration to the support medium.

2. The device according to claim 1 wherein the predetermined condition is selected from a preselected time, a sound originating from a location remote from the user, a signal from a safety or security device, an incoming telephone call, motion detected by a motion detection device, a bedwetting incident.

3. The device according to claim 2 wherein the safety or security device is selected from a smoke alarm, carbon monoxide detector, water or flood detector, burglar alarm, heart monitor, breathing monitor, infant monitor.

4. The device according to claim 2 wherein the existence of the predetermined condition is detected by a device separate from the selective alarm device which transmits a signal to the sensor/controller of the selective alarm device.

5. The device according to claim 2 wherein the signal to the sensor/controller is sent by wireless transmission.

6. The device according to claim 2 further comprising a timer for monitoring the vibrating time period after activation of the vibration mechanism and prior to termination of the vibration by the user.

7. The device according to claim 2 further comprising a supplemental alarm for transmitting notice to the user by one or more of audible, visible and olfactory media.

8. The device according to claim 7 wherein the supplemental alarm transmit notice to the user after the vibrating time period exceeds a predetermined time limit.

9. The device according to claim 1 or 4 wherein the controller is attached to the vibrating mechanism by a hardwire connection.

10. The device according to claim 1 wherein the vibrating mechanism is selected from a motor that rotates an eccentric weight in an electromagnetic field and a piezoceramic material which vibrates when an alternating voltage is applied.

11. The device according to claims 1 or 10 wherein the vibrating mechanism is capable of creating a range of vibration patterns differing in amplitude and/or frequency.

12. The device according to claim 1 wherein during the time period after activation by the controller the vibrating mechanism increases its amplitude and/or frequency of vibration to create a vibration pattern that is more stimulating in arousing the user.

13. The device according to claim 1 comprising a switch for the user to turn off the operation of the vibrating mechanism after activation.

14. The device according to claim 1 wherein the controller and vibration device are capable of providing a varying degree of intensity of vibrations to the user and which can be preprogrammed to provide a gradual increasing of intensity of vibrations until the vibration mechanism is turned off.

15. The device according to claim 1 further comprising a snooze alarm feature wherein after the user activates a snooze switch during the vibrating time period, the vibration terminates for a preselected time period after which the vibrating mechanism is activated.

16. The device according to claim 1 wherein the device further comprises a weight detecting element which shuts off the vibrating mechanism if the user is not detected as situated above the vibrating member.

17. The device according to claim 1 wherein the vibrating member is in the shape of a relatively flat pad ergonomically contoured for use under and adjacent the torso of a user.

18. The device according to claim 1 wherein the vibration transmission region of the vibrating member contains a material selected from the group consisting of soft, flexible synthetic rubber, visco-elastic gels and cross-linked polyurethane gels.

19. The device according to claim 1 wherein the vibration dampening region comprises a volume of material providing a continuous lower surface for the vibrating member.

20. The device according to claim 1 wherein the vibration dampening region comprises a plurality of discontinuous islands of material, each island associated with the location of a vibration mechanism in the vibrating member.

21. The device according to claim 1 wherein the vibration dampening region of the vibrating member contains an open-celled, flexible polymeric foam.

22. The device of claim 1 wherein the dampening region of the vibrating member comprises an open-celled, flexible polymeric foam having a density in the range of about 1.3 to about 1.8 pounds per cubic foot.

23. The device according to claim 1 wherein the vibrating member comprises a covering of a water-resistant or water-repellant material.

24. The device according to claim 1 wherein the vibration mechanism and other component parts are removable from the vibrating member.

25. The device according to claim 1 wherein the device contains at least two vibrating members and wherein they are not all controlled through a single control.

26. The device according to claim 1 which is sized and configured to independently alert or alarm two or more users situated on the same bed or support medium, comprising at least one vibrating member for each user, each vibrating member comprising one or more vibration mechanisms and associated regions of materials of varying density, each vibration mechanism configured to be located in the vicinity of the individual users on the bed or other support medium, each vibrating mechanism capable of vibrating at different amplitudes and frequencies.

27. The device according to claim 1 which is programmed to be an alarm clock for awakening a sleeping user on a bed at a pre-selected time without disturbing another person sleeping on the same bed, said device including a time keeping element and an alarm capable of accurately tracking and displaying time and capable of transmitting a signal to the vibrating mechanism when a preselected time coincides with the actual time on the time-keeping element.

28. The device of claim 1 wherein the vibrating mechanism is capable of creating a range of vibration patterns differing in amplitude and/or frequency which are controlled by the user and which provide the user with a massage of a portion of the user's body.

29. The device according to claim 28 further comprising a timer for monitoring the vibrating time period after activation of the vibration mechanism and prior to termination of the vibration by the user.

30. The device according to claim 28 wherein the vibration transmission region of the vibrating member contains a material selected from the group consisting of soft, flexible synthetic rubber, visco-elastic gels and cross-linked polyurethane gels.

31. The device according to claim 28 wherein the vibration dampening region comprises a volume of material providing a continuous lower surface for the vibrating member.

32. The device according to claim 28 wherein the vibration dampening region comprises a plurality of discontinuous islands of material, each island associated with the location of a vibration mechanism in the vibrating member.

33. The device according to claim 28 wherein the vibration dampening region of the vibrating member contains an open-celled, flexible polymeric foam.

34. The device of claim 31 wherein the dampening region of the vibrating member comprises an open-celled, flexible polymeric foam having a density in the range of about 1.3 to about 1.8 pounds per cubic foot.

35. The device according to claim 28 wherein the vibrating member comprises a covering of a vinyl or rubber material.

36. The device according to claim 28 wherein the surface facing away from the vibration mechanism contains a feature to maintain the vibrating member in a relatively fixed position with respect to the bed or support medium.

37. The device according to claim 28 wherein the device includes a backup alarm which is capable of being triggered when the user fails to turn off the device after a predetermined period of time after the vibration mechanism has been activated.

38. The device of claim 1 wherein the dampening region sufficiently reduces transmission of vibration to the surface of the vibrating member designated for facing the support medium to minimize transmission of vibration to any person other than the user on the support medium.

39. The device of claim 1 wherein the device has a configuration suitable for being located under the lower torso of a user situated on a support medium for transmission of vibration to the lower torso of the user.

* * * * *